(12) United States Patent
Park

(10) Patent No.: US 11,406,620 B2
(45) Date of Patent: Aug. 9, 2022

(54) USE OF CARBAMATE COMPOUND FOR PREVENTING OR TREATING DISEASES ASSOCIATED WITH INCREASE IN LATE SODIUM CURRENT

(71) Applicant: SK BIOPHARMACEUTICALS CO., LTD., Gyeonggi-do (KR)

(72) Inventor: Sun Young Park, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 136 days.

(21) Appl. No.: 16/763,642

(22) PCT Filed: Nov. 13, 2018

(86) PCT No.: PCT/KR2018/013753
§ 371 (c)(1),
(2) Date: May 13, 2020

(87) PCT Pub. No.: WO2019/098626
PCT Pub. Date: May 23, 2019

(65) Prior Publication Data
US 2020/0352908 A1    Nov. 12, 2020

(30) Foreign Application Priority Data
Nov. 14, 2017    (KR) .......................... 10-2017-0151243

(51) Int. Cl.
*A61K 31/41*    (2006.01)
*A61K 9/00*    (2006.01)

(52) U.S. Cl.
CPC ............ *A61K 31/41* (2013.01); *A61K 9/0019* (2013.01); *A61K 9/0031* (2013.01); *A61K 9/0053* (2013.01)

(58) Field of Classification Search
CPC .................................................. A61K 31/41
See application file for complete search history.

(56) References Cited

U.S. PATENT DOCUMENTS 10,456,376 B2 * 10/2019 Shin .................. A61P 25/06
10,849,882 B2 * 12/2020 Jo ........................ A61P 25/00
10,905,675 B2 * 2/2021 Pang .................... A61K 31/325
11,033,531 B2 * 6/2021 Yoo ...................... A61K 31/325
2012/0172363 A1    7/2012 Smith et al.

FOREIGN PATENT DOCUMENTS

| KR | 10-2008-0005437 A | 1/2008 |
|---|---|---|
| KR | 10-1708433 B1 | 2/2017 |
| WO | WO-2006/112685 A1 | 10/2006 |
| WO | WO-2009-015203 A1 | 1/2009 |
| WO | WO-2010/150946 A1 | 12/2010 |
| WO | WO-2011/046380 A2 | 4/2011 |

OTHER PUBLICATIONS

Bialer, M., et al.; "Progress report on new antiepileptic drugs: A summary of the Twelfth Eilat Conference (EILAT XII)", Epilepsy Research (2015) 111, 85-141.
International Search Report from corresponding PCT Application No. PCT/KR2018/013753, dated Feb. 19, 2019.
Extended European Search Report from corresponding European Patent Application No. 18878733.7, dated Jul. 6, 2021.
Hale, S. L., et al.; "Late sodium current inhibition as new cardioprotective approach", Journal of Molecular and Cellular Cardiology, 44, 2008, pp. 954-967.
Crumb, Jr., et al. (2016) "An evaluation of 30 clinical drugs against the comprehensive in vitro proarrhythmia assay (CiPA) proposed ion channel panel." *Journal of Pharmacological andToxicological Methods* 81:251 -262.
Makielski, J. (2009) "Late sodium current: a mechanism for angina, heart failure, and arrhythmia." *J Cardiovasc Pharmacol.*, 54(4):279-286. doi:10.1097/FJC.0b013e3181a1b9e7.
Makielski, J. MD. (2016) "Latesodiumcurrent:Amechanismfor angina, heart failure, and arrhythmia." *Trends in Cardiovascular Medicine*, 26:115-122.
Moreno, et al. (2012) "Pathophysiology of the cardiac late Na Current and its potential as a drug target." *J Mol Cell Cardiol.*, 52(3):1-29. doi:10.1016/j.yjmcc.2011.12.003.
Zaza, et al. (2008) "Pathophysiology and pharmacology of the cardiac "late sodium current".", *Pharmacology & Therapeutics*, 119:326-339.

* cited by examiner

*Primary Examiner* — Rei Tsang Shiao
(74) *Attorney, Agent, or Firm* — Harness, Dickey & Pierce, P.L.C.

(57) ABSTRACT

The present invention relates to a use of a carbamate compound of formula 1, or a pharmaceutically acceptable salt, solvate or hydrate thereof in the prevention or treatment of diseases associated with an increase in late sodium current.

10 Claims, 1 Drawing Sheet

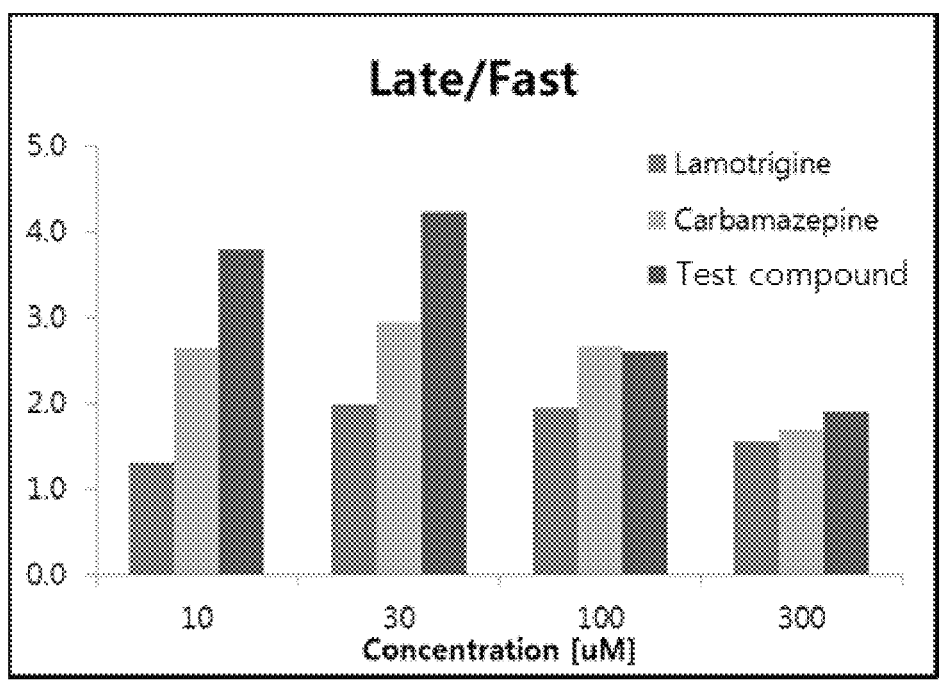

USE OF CARBAMATE COMPOUND FOR PREVENTING OR TREATING DISEASES ASSOCIATED WITH INCREASE IN LATE SODIUM CURRENT

CROSS-REFERENCE TO RELATED APPLICATIONS

This application is a national phase application of PCT Application No. PCT/KR2018/013753, filed on Nov. 13, 2018, which claims priority to Korean Patent Application No. 10-2017-0151243, filed on Nov. 14, 2017. The entire disclosure of the applications identified in this paragraph is incorporated herein by reference.

FIELD

The present invention relates to use of a carbamate compound of the following Formula 1, or a pharmaceutically acceptable salt, solvate or hydrate thereof for the prevention or treatment of diseases associated with an increase in late sodium current

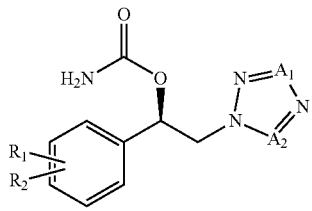

[Formula 1]

wherein,
$R_1$, $R_2$, $A_1$ and $A_2$ are as defined herein.

BACKGROUND

The sodium ion channel forms an action potential in the myocardial cell and is largely composed of fast (peak) current that affects the formation and propagation of action potentials and late current which serves to maintain and extend the action potential plateau when sodium ions penetrate through the non-inactivated ion channel. Late sodium current (INaL) can be pathologically increased by genetic or acquired heart disease.

Late sodium current is a persistent component of the fast sodium current of cardiomyocytes and neurons. An increase in late sodium current may be associated with a fundamental change or abnormality of the inactivation gate of the ion channel. An increase in late sodium current generally increases the likelihood of causing a Torsadogenic condition such as a prolonged repolarization and blocking of hERG K+(potassium ion channel affecting the repolarization process of action potentials). Certain nervous system and heart conditions are associated with abnormal increases in late sodium currents, which contribute to the pathogenesis of both electrical and contractile dysfunction in mammals (Pathophysiology and Pharmacology of the Cardiac "Late Sodium Current", Pharmacology and Therapeutics 119 (2008) 326-339).

In addition, when the late sodium current in cardiomyocytes increases, depolarization current also occurs in the plateau where the membrane voltage is kept high at the cardiac action potential, which leads to the prolongation of AP (action potential). AP prolongation leads to early after-depolarization at the cellular level and torsades de pointes (TdP) arrhythmia at the tissue/organ level.

Compounds that selectively inhibit late sodium current in mammals will be useful in treating these cardiovascular and neurological disease states.

There have been attempts to develop sodium ion channel inhibitors such as flecainide, lidocaine, amiodarone, etc. as therapeutic agents for heart disease due to an increase in late sodium current. However, most drugs failed because they could not selectively inhibit only late sodium current. Therefore, drugs for treating heart disease caused by an increase in the late sodium current can have safety and efficacy only by distinguishing the fast current and the late current. LQT3 syndrome (long QT3 syndrome) due to a congenital mutation of the sodium channels, arrhythmia and angina pectoris are known as diseases related to increase in late INa (late sodium current).

LQT3 syndrome is a disease that causes QT prolongation or arrhythmia, etc. due to an increase in late sodium current when there is a mutation in the SCN5A gene constituting Nav1.5 channel.

In case of angina pectoris, when the late sodium current increases in the ischemic myocardial state, the sodium concentration inside the cell increases, which causes an increase in the intracellular calcium concentration through sodium-calcium exchange. The increased intracellular calcium concentration prevents the heart from relaxing normally, which increases myocardial wall stress and end-diastolic pressure during the ventricular diastolic. As this situation repeats, ischemia in the subendocardial region gets worse. Drugs such as nitroglycerin, aspirin, Ranexa (Ranolazine), etc. or surgical therapy are used to treat angina pectoris (J. Cardiovasc Pharmacol. 2009 October; 54(4): 279-286. 10:1097/FJC.0b013e3181a11b9e7, J Mol Cell Cardiol. 2012 March; 52(3): 10.1016/j.yjmcc.2011.12.003, Trends in cardiovascular medicine 26(2016) 115-122, 10.1016/j.tcm.2015.05.006).

SUMMARY

Problem to be Solved

The present invention is intended to provide a method for the prevention or treatment of diseases associated with an increase in late sodium current.

The present invention is also intended to provide a method for the prevention or treatment of diseases associated with an increase in late sodium current in the heart.

The present invention is also intended to provide the use of a carbamate compound of the following Formula 1, or a pharmaceutically acceptable salt, solvate or hydrate thereof, for the prevention or treatment of diseases associated with an increase in late sodium current:

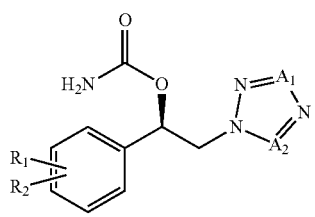

[Formula 1]

wherein,
$R_1$, $R_2$, $A_1$ and $A_2$ are as defined herein.

The present invention is also intended to provide the use of a carbamate compound of the above Formula 1, or a pharmaceutically acceptable salt, solvate or hydrate thereof, for the prevention or treatment of diseases associated with an increase in late sodium current in the heart.

Technical Solution to the Problem

The present invention provides a medicament for the prevention or treatment of diseases associated with an increase in late sodium current, comprising a therapeutically effective amount of a carbamate compound of the following Formula 1, or a pharmaceutically acceptable salt, solvate or hydrate thereof:

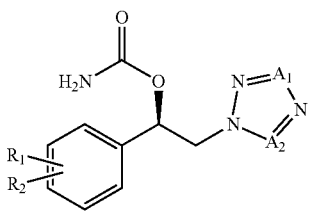

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

In addition, the present invention provides a pharmaceutical composition for the prevention or treatment of diseases associated with an increase in late sodium current, comprising a therapeutically effective amount of the carbamate compounds of the above Formula 1, or a pharmaceutically acceptable salt, solvate or hydrate thereof, and one or more of a pharmaceutically acceptable carrier.

In addition, the present invention provides a method for the prevention or treatment of diseases associated with an increase in late sodium current in a subject, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention or treatment of diseases associated with an increase in late sodium current.

In one embodiment of the present invention, in the above Formula 1, $R_1$ and $R_2$ are each independently selected from the group consisting of hydrogen, halogen and $C_1$-$C_8$ alkyl.

In one embodiment of the present invention, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

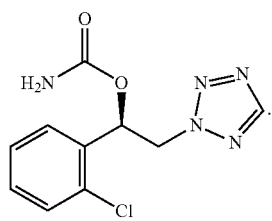

[Formula 2]

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the present invention can be chemically synthesized by any of the methods described in the above documents, but the methods are merely exemplary ones, and the order of the unit operation and the like may be selectively changed if necessary. Hence, the above methods are not intended to limit the scope of the invention.

In one embodiment of the present invention, the carbamate compound of Formula 1, or a pharmaceutically acceptable salt, solvate or hydrate thereof inhibits the late sodium current (INaL) more selectively than the fast sodium current, which is specifically confirmed in the examples described below.

In one embodiment of the present invention, the disease associated with the increase in the late sodium current may be a neurological disease or a cardiovascular disease. Specifically, a disease associated with an increase in late sodium current may be a disease associated with an increase in late sodium current in the heart.

The carbamate compound of Formula 1 may be used for the prevention or treatment of diseases associated with an increase in the late sodium current in the heart. In one embodiment of the present invention, examples of diseases associated with an increase in late sodium current in the heart include, but are not limited to, long QT3 syndrome, arrhythmia, angina pectoris, atrial fibrillation, ventricular tachycardia, ventricular fibrillation, heart failure and hypertrophic cardiomyopathy. More specifically, diseases associated with an increase in the late sodium current in the heart are particularly long QT3 syndrome, arrhythmia or angina pectoris.

Long QT syndrome or LQT syndrome is caused by dysfunction of protein structures called ion channels in heart cells and protein structures that modulate the activity of ion channels. These channels control the flow of ions such as potassium, sodium and calcium molecules. The flow of these ions inside and outside the cells creates the electrical activity of the heart. Abnormalities in these channels can be acquired or inherited.

The genetic form of long QT syndrome occurs when a mutation occurs in one of several genes that produce or encode one of the ion channels or ion channel modulators that control electrical repolarization. Of these, in particular, the long QT3 syndrome results from mutations in the SCN5A gene. In one embodiment of the present invention, the symptoms of the long QT3 syndrome may be selected from, but are not limited to, the group consisting of abnormal heartbeat, subsequent fainting, seizures and sudden death.

Arrhythmia refers to any abnormal heart rate. Bradycardia refers to an abnormally slow heart rate, while tachycardia refers to an abnormally fast heart rate. In the present specification, treatment of arrhythmia is intended to include treatment of ventricular tachycardia (VT) comprising supraventricular tachycardia—for example, atrial fibrillation, atrial flutter, AV nodular recurrent tachycardia, atrial tachycardia and idiopathic ventricular tachycardia, ventricular fibrillation, early excitation syndrome and torsades de pointes (TdP). In one embodiment of the present invention, the symptoms of arrhythmia may be selected from, but are not limited to, the group consisting of slight palpitations, chest pain, syncope and sudden death.

In angina pectoris, when the late sodium current increases in the ischemic myocardial state, the sodium concentration inside the cells increases, which leads to an increase in the intracellular calcium concentration through sodium-calcium exchange. The increased intracellular calcium concentration prevents the heart from relaxing normally, which increases myocardial wall stress and end-diastolic pressure during the ventricular diastolic. As this situation repeats, ischemia in the subendocardial region intensifies. As used herein, treatment of angina pectoris is intended to include treatment of stable angina, unstable angina and exercise-induced angina.

The dosage of the carbamate compounds of Formula 1 for the prevention or treatment of the above diseases may typically vary depending on the severity of the disease, the body weight and the metabolic status of the subject. A "therapeutically effective amount" for an individual patient refers to an amount of the active compound sufficient to achieve the above pharmacological effect—i.e., the therapeutic effect as described above. The therapeutically effective amount of the compounds of the present invention is 50 to 500 mg, 50 to 400 mg, 50 to 300 mg, 100 to 400 mg, 100 to 300 mg, 50 to 200 mg or 100 to 200 mg, based on the free form and once-daily administration to humans.

The compounds of the present invention can be administered by conventional methods used for administration of therapeutic agents, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the above compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated such that the active agent is coated or it is protected against degradation in the stomach. In addition, the composition can be administered by any device capable of transferring the active substance to target cells. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses—for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg or 100 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the term "subject" refers to an animal that is the object of prevention or treatment, preferably a mammal (such as primates (e.g., humans), cattle, sheep, goats, horses, dogs, cats, rabbits, rats, mice, etc.), most preferably a human.

As used herein, the terms "prevent," "preventing" and "prevention" refer to reducing or eliminating the likelihood of a disease.

As used herein, the terms "treat," "treating" and "treatment" refer to eliminating a disease and/or its accompanying symptoms altogether or in part.

Effect of the Invention

The compounds of the present invention show an effect of inhibiting the late sodium current more selectively than the fast sodium current, and thus show safety and differentiation compared to the existing drugs in the treatment of diseases associated with an increase in the late sodium current in the heart. Accordingly, the medicament and pharmaceutical composition according to the present invention can effectively prevent and treat diseases associated with an increase in late sodium current, specifically diseases associated with an increase in late sodium current in the heart, more specifically, long QT3 syndrome, arrhythmia, angina pectoris, atrial fibrillation, ventricular tachycardia, ventricular fibrillation, heart failure and hypertrophic cardiomyopathy.

BRIEF DESCRIPTION OF THE DRAWINGS

FIG. 1 shows the inhibition rate by concentration at each of the fast sodium current and the late sodium current of carbamic acid (R)-1-(2-chlorophenyl)-2-tetrazol-2-yl-ethyl ester (hereinafter referred to as "test compound") prepared in the Preparation Example and a control compound.

DETAILED DESCRIPTION

Hereinafter, the present invention will be explained in more detail through working examples. However, the following working examples are only intended to illustrate one or more embodiments and are not intended to limit the scope of the invention.

Preparation Example: Synthesis of Carbamic Acid (R)-1-(2-chlorophenyl)-2-tetrazol-2-yl-ethyl Ester Carbamic acid (R)-1-(2-chlorophenyl)-2-tetrazol-2-yl-ethyl ester (the test compound) was prepared according to the method described in Preparation Example 50 of PCT Publication No. WO 2010/150946.

Example 1: Electrophysiology Experiments on the Inhibitory Effect of an Increase in Late Sodium Current in the Heart In order to confirm the effect of the test compound prepared in the above Preparation Example on the fast current and the late current of the naïve human recombinant sodium ion channel Nav1.5 (hNav1.5), the whole cell patch clamp technique was used (Journal of pharmacological and Toxicological methods 81 (2016) 251-262, 10.1016/j.vascn.2016.03.009). To study the nocturnal Nav1.5 channel, a cell line stably expressing SCNASA (Gene ID: 6331, https://www.ncbi.nlm.nih.gov/gene/6331) encoding a human Nav1.5 channel in HEK293 cells was used.

Pulse-protocol was used to measure the effect of the test compound on the Nav1.5 channel at the fast current and the late current, and through this, the difference in the degree of inhibition of the compound against the fast current and the late current was confirmed. Since the late current shows a significantly smaller current size than the fast current, measurement was performed after adding 10 uM of late sodium current activator veratridine to the external solution in order to increase it. Pulse-protocol uses a protocol that gives a −15 mV stimulus for 385 ms at a holding voltage of −120 mV, and then returns to a holding voltage of −120 mV, and the current generated with the −15 mV stimulus (fast current) and the current just before returning to −120 mV (late current) was measured. By applying a pulse-protocol configured in this way in 10-second intervals (0.1 Hz), the inhibitory effect of the drug on the fast current and the late current was confirmed.

The composition of the external solution used in the experiment is as follows: 137 mM NaCl, 4 mM KCl, 1.8 mM $CaCl_2$) mM, 1 mM $MgCl2$, 10 mM HEPES, 11 mM D-Glucose, pH 7.4 (NaOH), 280 mOsm.

The composition of the internal solution used in the experiment is as follows: 130 mM CsCl, 1 mM $MgCl2$, 7 mM NaCl, 5 mM HEPES, 5 mM EGTA, pH 7.2 (CsOH), 270 mOsm.

TABLE 1

Degree of inhibition of the fast and late current of each drug (%)

| Concentration (μM) | Test compound | | Carbamazepine | | Lamotrigine | |
|---|---|---|---|---|---|---|
| | Fast | Late | Fast | Late | Fast | Late |
| 10 | 3.0% | 11.4% | 7.7% | 20.4% | 8.3% | 10.7% |
| 30 | 5.7% | 24.0% | 12.3% | 36.2% | 16.6% | 32.9% |
| 100 | 13.0% | 33.9% | 24.5% | 65.4% | 29.0% | 56.7% |
| 300 | 26.2% | 49.8% | 51.4% | 86.9% | 51.2% | 80.1% |

TABLE 2

Inhibition ratio of late current/fast current of each drug

| Concentration (μM) | Test compound | Carbamazepine | Lamotrigine |
|---|---|---|---|
| 10 | 3.8 | 2.6 | 1.3 |
| 30 | 4.2 | 2.9 | 2.0 |
| 100 | 2.6 | 2.7 | 2.0 |
| 300 | 1.9 | 1.7 | 1.6 |

Carbamazepine and lamotrigine, used as comparative compounds, are known to inhibit the sodium channel of the heart. Table 1 shows the degree of inhibition (%) of the fast current and late current by concentration of the test compound and the comparative compounds (controls), and Table 2 shows the inhibition ratio of late current/fast current by concentration of each drug. According to the results in Table 2, it was found that the test compound inhibited the late sodium current more selectively than the fast sodium current at a concentration in the drug effective concentration range compared to the comparative compounds. Therefore, the test compound can be used to alleviate symptoms such as LQT3 syndrome, arrhythmia, angina pectoris, etc., which are manifested by an increase in late sodium current, and can be said to show safety and differentiation compared to drugs used as controls because it inhibits late sodium current more selectively.

What is claimed is:

1. A method for the treatment of diseases associated with an increase in late sodium current in the heart selected from the group consisting of long QT3 syndrome, arrhythmia, angina pectoris, atrial fibrillation, ventricular tachycardia, ventricular fibrillation, heart failure and hypertrophic cardiomyopathy, comprising administering a therapeutically effective amount of a carbamate compound of the following Formula 1, or a pharmaceutically acceptable salt, solvate or hydrate thereof to a subject in need thereof:

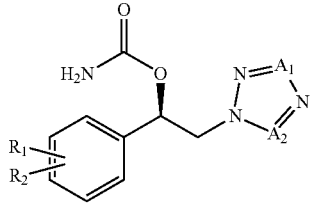

[Formula 1]

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-2-tetrazol-2-yl-ethyl ester of the following Formula 2:

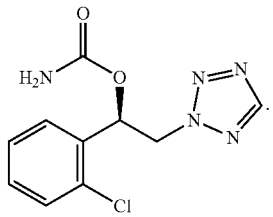

[Formula 2]

4. The method according to claim 1, wherein the disease associated with an increase in late sodium current in the heart is long QT3 syndrome, arrhythmia or angina pectoris.

5. The method according to claim 4, wherein the symptom of long QT3 syndrome is selected from the group consisting of an abnormal heartbeat, subsequent fainting, seizures and sudden death.

6. The method according to claim 4, wherein the symptom of arrhythmia is selected from the group consisting of slight palpitations, chest pain, syncope and sudden death.

7. The method according to claim 1, which is for mammalian administration.

8. The method according to claim 7, wherein the mammalian is a human.

9. The method according to claim 1, wherein the therapeutically effective amount of the carbamate compound of Formula 1 is 50 to 500 mg based on once-daily administration on the free forms.

10. The method according to claim 1, which is for oral, parenteral, intravenous, intramuscular, subcutaneous or rectal administration.

* * * * *